US008765967B2

(12) United States Patent
Berg-Schultz

(10) Patent No.: US 8,765,967 B2
(45) Date of Patent: Jul. 1, 2014

(54) MICROCAPSULES WITH UV FILTER ACTIVITY AND PROCESS FOR PRODUCING THEM

(75) Inventor: Katja Berg-Schultz, Kalseraugst (CH)

(73) Assignee: DSM IP Assets B.V., Te Heerlen (NE)

(*) Notice: Subject to any disclaimer, the term of this patent is extended or adjusted under 35 U.S.C. 154(b) by 16 days.

(21) Appl. No.: 13/195,991

(22) Filed: Aug. 2, 2011

(65) Prior Publication Data
US 2012/0022265 A1 Jan. 26, 2012

Related U.S. Application Data

(63) Continuation of application No. 10/581,511, filed as application No. PCT/EP2004/013734 on Dec. 2, 2004, now abandoned.

(30) Foreign Application Priority Data

Dec. 4, 2003 (EP) .................................. 03027847

(51) Int. Cl.
C07F 7/18 (2006.01)
A61K 8/00 (2006.01)

(52) U.S. Cl.
USPC ..... 548/110; 556/445; 428/402.1; 428/402.4; 424/401; 424/59

(58) Field of Classification Search
USPC .................. 548/110, 112; 556/445;
428/402–402.24, 403, 404, 407;
427/389.9, 213.3–213.36, 483, 256;
264/534, 41, 4–4.7; 424/400, 408, 450,
424/451, 455, 93.7, 184.1, 497, 489, 501,
424/490, 491, 492, 493, 494, 495
See application file for complete search history.

(56) References Cited

U.S. PATENT DOCUMENTS

| 5,254,542 | A | * | 10/1993 | Sakuta et al. | .................. 514/63 |
| 6,123,928 | A | | 9/2000 | Sovak et al. | |
| 6,159,453 | A | * | 12/2000 | Avnir et al. | .................. 424/59 |
| 6,607,713 | B1 | | 8/2003 | Chodorowski et al. | |
| 2002/0037261 | A1 | | 3/2002 | Lapidot et al. | |

FOREIGN PATENT DOCUMENTS

| EP | 0 478 284 | 4/1992 |
| WO | 98/31333 | 7/1998 |

OTHER PUBLICATIONS

Efimov et al., "Synthesis of Organosilicon Derivatives of Acrylic Acids," Journal of General Chemistry USSR, vol. 61, No. 10, part 2, pp. 2083-2091 (1991).
Morais et al., "Communications: Hybrid Organic-Inorganic Light-Emitting Diodes," Advanced Materials, vol. 11, No. 2, pp. 107-112 (1999).
Pandey et al., "On the Microenvironments Surrounding Dansyl Sequestered Within Class I and II Xerogels," Chem. Mater., vol. 12, pp. 3547-3551 (2000).
Spange et al., "A One-Pot Synthesis of Chromophoric Silicate-Based Xerogels," Angew. Chem. Int. Ed., vol. 41, No. 10, pp. 1729-1732 (2002).
Kachiuchi et al., [online] Database Beilstein Online!, Abstract No. XP002327220, Database accession No. 7217707 [data entered on Oct. 31, 1995, updated on Nov. 1, 1995].
Mironov et al., [online] Database Bellstein Online!, Abstract No. XP002327221, Database accession Nos. 515138, 521986 [data entered on Nov. 28, 1988, updated on Feb. 26, 1992].
Sheludyakov et al., [online] Database Beilstein Online!, Abstract No. XP002327222, Database accession Nos. 920180, 521809 [data entered on Nov. 28, 1988, updated on Feb. 26, 1992].
Voronkov et al., [online] Database Beilstein Online!, Abstract No. XP002327223, Database accession No. 8830008 [data entered on Oct. 25, 2001].
Varma et al., [online] Database Beilstein Online!, Abstract No. XP002327224, Database accession No. 5949952 [data entered on Jul. 22, 1993, updated on Jan. 3, 1996].
Samartseva et al., [online] Database Beilstein Online!, Abstract No. XP002327225, Database accession No. 1115032 [data entered on Nov. 29, 1988, updated on Jan. 21, 2005].
Bayer, [online] Database Beilstein Online!, Abstract No. XP002327226, and Database accession No. 1111557 [data entered on Nov. 29, 1988, updated on Oct. 7, 1992].
Passerini et al., [online] Database Beilstein Online!, Abstract No. XP002327227 and Database accession No. 162744 [data entered on Jun. 27, 1988, updated on Jul. 19, 1994].
Breukelman et al., [online] Database Beilstein Online!, Abstract No. XP002327228, Database accession No. 5086309 [data entered on Aug. 28, 1992, updated on Mar. 20, 1993].
Chrzaszczewska et al., [online] Database Beilstein Online!, Abstract No. XP002327229, Database accession No. 2700680 [data entered on Jul. 5, 1989, updated on Jan. 21, 2005].
Kelemen et al., [online] Database Beilstein Online!, Abstract No. XP002327230, Database accession No. 1283047 [data entered on Nov. 29, 1988, updated on Feb. 25, 1992].
Ohta et al., [online] Database Beilstein Online!, Abstract No. XP002327231, Database accession No. 127823 [data entered on Jun. 27, 1988, updated on Jan. 21, 2005].
Oka et al., [online] Database Beilstein Online!, Abstract No. XP002327232, Database accession No. 1121647 [data entered on Nov. 29, 1988, updated on Feb. 20, 1996].
Sorm et al., [online] Database Beilstein Online!, Abstract No. XP002327233, Database accession No. 176436 [data entered on Jun. 27, 1988, updated on Oct. 23, 2004].

(Continued)

Primary Examiner — James J Seidleck
Assistant Examiner — S. Camilla Pourbohloul
(74) Attorney, Agent, or Firm — Bryan Cave LLP

(57) ABSTRACT

The invention provides a process for producing microcapsules with UV filter activity, wherein at least one type of crosslinkable chromophore with UV-A and/or UV-B and/or UV-C filter activity and optionally at least one type of crosslinkable monomer which does not have UV-A and/or UV-B and/or UV-C filter activity are subjected to a crosslinking reaction in the absence of non-crosslinkable chromophores with UV-A and/or UV-B and/or UV-C filter activity and microcapsules obtainable by this process.

9 Claims, No Drawings

(56) References Cited

OTHER PUBLICATIONS

Profft et al., [online] Database Beilstein Online!, Abstract No. XP002327234, Database accession No. 162675 [data entered on Jun. 27, 1988, updated on Nov. 1, 1995].

Geigy, [online] Database Beilstein Online!, Abstract No. XP002327235, Database accession No. 537844 [data entered on Nov. 28, 1988, updated on May 13, 1992].

Elbs, [online] Database Beilstein Online!, Abstract No. XP002327236, Database accession No. 226966 [data entered on Jun. 27, 1988, updated on Jan. 3, 1996].

Haller et al., [online] Database Beilstein Online!, Abstract No. XP002327237, Database accession No. 3206755 [data entered on Feb. 15, 1990, updated on Jun. 2, 1992].

Hancock et al., [online] Database Beilstein Online!, Abstract No. XP002327238, Database accession No. 2099994 [data entered on Jun. 29, 1989, updated on Apr. 17, 2003].

Safety data for tetraethyl orthosilicate, [online] [retrieved on Nov. 9, 2010] Retrieved from http://msds.chem.ox.ac.uk/TE/tetraethyl_orthosilicate_html.

Material Safety Data Sheet, Matheson TriGas, [online] [retrieved on Nov. 9, 2010] retrieved from www.smfl.rit.edu/pdf/msds/msds_teos.pdf.

\* cited by examiner

MICROCAPSULES WITH UV FILTER ACTIVITY AND PROCESS FOR PRODUCING THEM

RELATED APPLICATIONS

This application is a continuation of U.S. patent application Ser. No. 10/581,511, filed Jun. 1, 2006. The '511 application is a national stage of International Application No. PCT/EP2004/013734, filed Dec. 2, 2004, which claims priority to EP Application No. 03027847.7, filed Dec. 4, 2003.

FIELD OF THE INVENTION

The present invention relates to novel UV filters on the basis of microcapsules, a process for the preparation and their use especially in formulations for the protection against harmful effects of sunlight.

BACKGROUND OF THE INVENTION

There is a constantly increasing need for sunscreen protection agents in a population that is exposed to an increasing amount of damaging sunlight. Repetitive sun exposure can result in skin changes known as photoaged skin. The clinical changes that are seen in photoaged skin differ from those of normally aged skin in sunlight protected sites of the body. Among the damaging results of intensive sun exposure of the skin there is increased wrinkling, elastosis, pigmentary changes, precancerous and cancerous skin lesions.

Many sunscreening chemicals have been developed in the past protecting against the harmful effect of UV-A (320 to 400 nm) and/or UV-B (290-320 nm) wavelength and even shorter wavelength (UV-C). These chemicals are usually incorporated either alone or in combination with each other into cosmetic or pharmaceutical preparations which are widely known and used.

BRIEF SUMMARY OF THE INVENTION

Most UV filters used in sunscreen compositions are monomeric compounds e, and thus there is the inherent risk that such compounds can penetrate the skin barrier, which is highly undesirable. UV filters on the basis of polysiloxanes which may be either linear or cyclic are described e.g. in WO 93/04665, WO 94/06404, EP-A 538 431, EP-A 392 883 and EP-A 358 584. With these polysiloxanes the risk of skin penetration is lower, but it is sometimes difficult to incorporate the polysiloxanes in sunscreen compositions due to incompatibility problems which differ depending on the UV-active chromophores which are covalently bonded to the polysiloxanes.

A further problem with presently known UV filters is that they tend to interact, which in some cases in which a sunscreen composition contains more than one type of UV filter, leads to a situation where the UV filter activity of one or both of the UV filters is reduced during storage or after being applied to the skin. Attempts have been made to solve this problem by encapsulating one type of UV filter or two or more types of UV filter which are present in a sunscreen composition in order to minimize the contact of the UV filters during storage and when applied to the skin. Microcapsules are disclosed which release the UV filters over time, others are designed to permanently encapsulate the UV filter. Encapsulation technologies are described e.g. in FR 2 642 329, DE-A 195 37 415, EP-A 509 904, FR 2 726 760 and FR 2 687 914 as well as WO 00/71084, U.S. Pat. No. 6,303,149, WO 98/31333, U.S. Pat. No. 5,876,699 and WO 00/72806.

Some of these microencapsulated UV filters are designed to release the UV filter from the microcapsules in a controlled manner in order to maintain a constant concentration of the UV filter in the sunscreen composition. Thus, the active UV filters in the sunscreen compositions are still highly movable monomeric compounds which have the inherent risk of penetrating the skin after application. Furthermore, in these embodiments there may still be inactivation of the UV filters, and in order to maintain a constant concentration in a sunscreen composition, the microcapsules need to have a high initial loading. Finally, it is difficult to ensure a controlled release of the UV filters from the microcapsules.

In another embodiment microcapsules are designed which should permanently encapsulate the UV filters and those microcapsules are often prepared by a sol-gel process. However, it is difficult to prepare microcapsules which do not leak the UV filters, and in practice it has been shown that the interaction between the UV filters can be reduced by encapsulating them e.g. with a sol-gel process, but this only slows down the inactivation of the UV filters but does not sufficiently prevent it.

WO 98/31333 discloses sunscreen doped sol-gel materials which are useful for protecting body tissue and other surfaces from sunlight radiation. The sol-gel materials are prepared by encapsulating UV filter chromophores by a sol-gel process. It is also disclosed that the monomers which are used for encapsulating the chromophores can be compounds of a general formula $M(R)_n(P)_m$, wherein M is a metallic or semi-metallic element, R is a hydrolysable substituent, n is an integer from 2 to 6, P is a non-polymerizable substituent or sunscreening moiety and m is an integer from 0 to 6. Thus, this document considers the possibility to use monomers for the formulation of the matrix of the microcapsules which in themselves have sunscreening activity (without disclosing any example of such a monomer). However, these monomers are still used to form a matrix which encapsulates monomeric chromophores which are not covalently bonded to the matrix material and in all processes for producing microcapsules disclosed in this document monomeric non-polymerizable chromophores are encapsulated by the sol-gel process. Thus, the microcapsules disclosed in WO 98/31333 all comprise encapsulated chromophores which are not chemically bonded to the matrix material, and it was obviously believed that it is not possible to provide microcapsules with sufficient sunscreen activity, if no chromophores are encapsulated within the microcapsules. Accordingly, the microcapsules disclosed in WO 98/31333 still show the problems discussed above.

EP-A 1 205 178 and EP-A 1 205 177 suggest to reduce the risk of penetration of active ingredients such as UV filters into the skin and possible damage of the skin or allergies caused thereby by immobilizing the active ingredients or UV filters present in a dermatological or cosmetic composition. These documents disclose a conjugate which comprises an anorganic pigment and an active ingredient on the basis of an organic compound which is covalently bonded via a spacer group to the anorganic pigment. The conjugate disclosed in these documents thus contains an anorganic pigment and to the surface of this pigment chromophores are chemically bonded. With such a construction the problem of penetration of the active ingredient into the skin is solved, however, there is still the risk that the active ingredients interact with one another, which can lead to a deactivation of the UV filter activity in the lightscreening composition, because all chromophores are on the surface of the anorganic pigment.

The problem to be solved by the present invention is the provision of novel UV filters which do not show the shortcomings of the prior art as described above. The UV filters should have excellent UV filter activity, be easily accessible and compatible with the other usual ingredients of cosmetic and dermatological compositions.

It was surprisingly found that a new type of UV filters which is in the form of microcapsules and obtainable by a process, wherein at least one type of crosslinkable monomer with UV-A and/or UV-B and/or UV-C filter activity and optionally at least one type of crosslinkable monomer which does not have UV-A and/or UV-B and/or UV-C filter activity are subjected to a crosslinking reaction in the absence of non-crosslinkable chromophores with UV-A and/or UV-B and/or UV-C filter activity.

Contrary to the belief in the prior art which is expressed e.g. in WO 98/31333, it was found that microcapsules which exclusively comprise chromophores with UV filter activity which are covalently bonded to the polymer matrix of the microcapsule have sufficient UV filter activity and that it is not necessary to dope these microcapsules with additional monomeric chromophores which are not covalently bonded to the polymeric matrix material but encapsulated in the microcapsules. Therefore, the microcapsules of the present invention do not comprise encapsulated monomeric chromophores with UV filter activity, but all chromophores which are present in the microcapsules of the present invention are covalently bonded to the polymer which forms the matrix material.

DETAILED DESCRIPTION OF THE INVENTION

The term "UV filter activity" as used herein encompasses UV-A, UV-B and UV-C filter activity, preferably UV-A and UV-B filter activity. If the term "UV filter" or "UV filter activity" is used without further explanation, it refers to compounds or compositions or moieties which have either UV-A or UV-B or UV-C filter activity as well as to compounds or compositions or moieties which have both UV-A and UV-B filter activity and to compounds or compositions or moieties which have UV-A, UV-B and UV-C filter activity and to compounds or compositions or moieties which have both UV-B and UV-C filter activity. Preferably, the term "UV filter" or "UV filter activity" is used for compounds, compositions or moieties which have UV-A or UV-B filter activity or for compounds, compositions or moieties which have both UV-A and UV-B filter activity.

The present invention is also directed to the process for producing these novel microcapsules with UV filter activity, to sunscreen compositions comprising the microcapsules and to the use of the microcapsules for producing a sunscreen composition.

The present invention employs methods of preparing microcapsules which are well known in the art and which have in the past been used to prepare encapsulated UV filters. However, contrary to the prior art technology, according to the present invention all compounds with UV filter activity are covalently bonded to the monomers which form the matrix of the microcapsules. The novel UV filters in the form of microcapsules combine several advantages which could not be achieved with the UV filters of the prior art. In particular a leakage of the monomeric UV filters causing the risk of penetration into the skin and allergic reactions or skin diseases no longer exists. Furthermore, since most of the chromophores with UV filter activity are covalently bonded within the microcapsules and only a small amount of the chromophores with UV filter activity is present on the surface of the microcapsules, there is no risk that a significant number of the UV filter-active sites of the microcapsules come into contact with non-compatible components such as other UV filter-active molecules, which might lead to an inactivation of the UV filter activity, a problem which still occurs with the UV filters disclosed in EP-A 1 205 177 and EP-A 1 205 178.

An important feature of the microcapsules of the present invention and the process for producing them is that no monomeric non-crosslinkable chromophores having UV filter activity are present during the formation of the microcapsules, e.g. during the sol-gel process. Thus, it is ensured that all chromophores with UV filter activity which are present in the so prepared microcapsules are covalently bonded to the polymeric matrix of the microcapsules. There might be a minor amount of contamination by unreacted crosslinkable chromophores which is not relevant for the invention and should be avoided as far as possible. Preferably the microcapsules of the present invention do not contain any unreacted crosslinkable chromophores with UV filter activity.

The crosslinkable chromophores with UV filter activity are novel compounds, and the present invention is also directed to those crosslinkable chromophores.

The type of crosslinkable chromophore with UV filter activity according to the present invention is not particularly limited. Most preferred are chromophores of the formula $M(R)_n(P)_m(Q)_q$, wherein M is a metallic or semi-metallic element (such as silicon, titanium, zinc, aluminum or zirconium, preferably silicon), preferably, M is silicon R is a hydrolysable substituent with preferably not more than 10 carbon atoms (such as an alkoxide, aryloxide, carboxylic ester, acyloxy group, diketonato group, hydrolysable aza group or chlorine), more preferably an alkoxide or an acyloxy group with not more than 10 carbon atoms, in particular a $C_1$-$C_6$ alkoxide such as a methoxide or an ethoxide Q is a non-hydrolysable group, preferably a hydrocarbon group with not more than 10 carbon atoms, such as a $C_1$-$C_6$ alkyl group, e.g. a methyl or ethyl group, n is an integer of 2 or 3, preferably 3, m is an integer of 1 or 2, and q is an integer of 0 or 1 and n+m+q=4.

P is the moiety of the molecules which provides the UV filter activity and preferably has a general formula $A\text{-}(B)_b(C)_c(D)_d(E)_e$—which is chemically bonded to M wherein A is a chromophore with UV-A and/or UV-B filter activity and -$(B)_b(C)_c(D)_d(E)_e$—is a spacer group in which B is a linear or branched alkylene group with up to 20, preferably 1-12, most preferred 3-12 carbon atoms C is O, S or NH D is a CONH— group E is a linear or branched alkylene or alkenylene group with up to 20, preferably 1-12, most preferred 3-12 carbon atoms and b is 0 or 1, c is 0 or 1, d is 0 or 1 and e is 0 or 1.

Preferably, M is silicon, R has not more than 10 carbon atoms and is an alkoxide, an aryloxide or an acyloxy group, more preferably an alkoxide or an acyloxy group with not more than 10 carbon atoms, in particular a $C_1$-$C_6$ alkoxide such as a methoxide or an ethoxide, n is an integer of 2 or 3, in particular of 3, P is a residue A with UV-A and/or UV-B filter activity which is chemically bonded to M usually by a spacer group (P is the combination of A and the spacer group) and m is 1. The spacer group has preferably 1 to 10 carbon atoms and optionally 1 to 3 hetero atoms such as nitrogen or oxygen atoms and is preferably of the formula -$(B)_b(C)_c(D)_d$ $(E)_e$—as defined above.

The preparation of crosslinkable chromophores with UV filter activity is within the knowledge of the skilled person who knows the present specification, and some preferred examples are generally disclosed in the following:

Addition of an hydroxyl or amino-terminated molecule A on the 3-(isocyanatopropyl)triethoxysilane (ICPTEOS) resulting in a carbamate or urethane link;

Amidation of an acyl chloride-terminated molecule M using the 3-(aminopropyl)-triethoxysilane (APTEOS).

Nucleophilic substitution of a chlorine such as in 3-(chloropropyl)-triethoxysilane (CPTEOS) with a primary or secondary amine whereas the amine can be member of a heterocyclic ring.

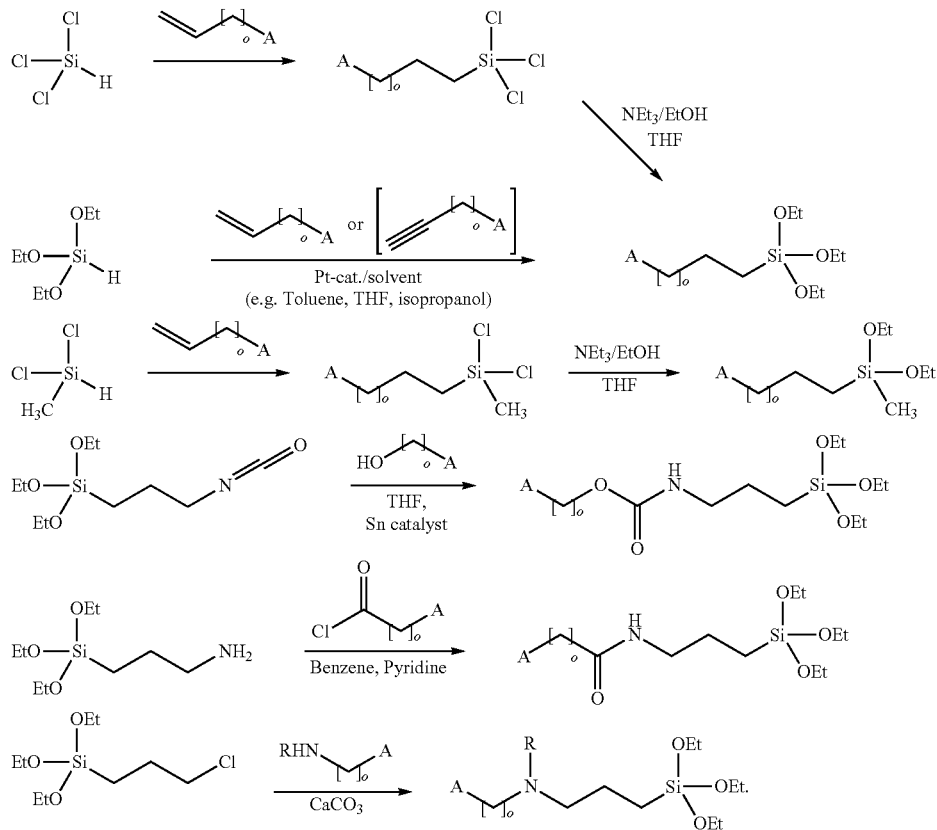

In the above scheme residue A is the part of the residue P which provides the UV filter activity, and residue P usually consists of a residue A and optionally a spacer group which is used for coupling the residue A to the metal or semi-metal M, in particular to the silicon, index o is 0 to 6, preferably 0, 1, 2 or 3.

In the above scheme preferred embodiments of the invention have been exemplified in which residue M is silicon, and all residues R are chlorine or an ethoxide. Embodiments in which n is 3 and m is 1 are particularly preferred. Of course, the processes are also applicable for other embodiments, in particular for other alkoxides.

The residues A are preferably known UV light absorbers, and these known UV light absorbers are modified preferably by a functional silanes such as methyldichlorosilane, trichlorosilane, triethoxysilane, 3-(isocyanatopropyl)triethoxysilane, or 3-(chloropropyl)triethoxysilane or 3-(aminopropyl)-triethoxysilane without being limited thereto e.g. by Hydrosilylation between an allyl or propargyl-terminated molecule A and triethoxysilane, methyldichlorosilane (MDCIS) or the trichlorosilane (TCIS). This coupling reaction results in a C—Si bond;

The UV-light absorbing groups A covalently bonded to the microcapsules comprise all groups which absorb light in the range of wavelengths 400-320 nm (UVA) and 320-290 (UVB) or of even shorter wavelengths (UVC) and which are or can be used as chemical UV filters. These groups are, e.g., residues of compounds belonging to the groups of acrylates, p-aminobenzoates, camphor derivatives (such as of benzylidene camphor type), cinnamates, benzophenones, esters of benzalmalonic acid, esters of 2-(4-ethoxy anilinomethylene)propandioic, imidazole derivatives, salicylates, triazone derivatives, triazol derivatives, dibenzoylmethanes, amino substituted hydroxybenzophenones, phenyl-benzimidazoles, anthranilates, phenyl-benzoxazoles, 1,4-dihydropyranes and others representing state of the art and known to those skilled in the art to be highly active.

Examples for acrylates include 2-ethylhexyl 2-cyano-3,3-diphenylacrylate (octocrylene, PARSOL® 340) and ethyl 2-cyano-3,3-diphenylacrylate;

Examples for p-aminobenzoates include 4-amino benzoic acid, 4-aminobenzoic acid-2,3-dihydroxypropylester, 4-(bis (2-hydroxypropyl)amino)benzoic acid ethyl ester, 4-(dimethylamino)benzoic acid-2-ethylhexylester (e.g. Eusolex® 6007) and ethoxylated 4-aminobenzoic acid ethyl ester (e.g. Uvinul® P25).

Examples for camphor derivatives include 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor and therephthalidene dicamphor sulfonic acid;

Examples for cinnamates include octyl methoxycinnamate (PARSOL® MCX), ethoxyethyl methoxycinnamate, diethanolamine methoxycinnamate (PARSOL® Hydro) and isoamyl methoxycinnamate.

Examples for benzophenones include benzophenone-3, benzophenone-4, 2,2',4,4'tetrahydroxy-benzophenone and 2,2'Dihydroxy-4,4'dimethoxybenzophenone;

Examples for esters of benzalmalonic acid include di(2-ethylhexyl)4-methoxy-benzalmalonate Examples for esters of 2-(4-ethoxy anilinomethylene)propandioic acid include 2-(4-ethoxy anilinomethylene)propandioic acid diethyl ester as described in the European Patent Publication EP 0895 776

Examples for imidazole derivatives include 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts and diethanolamine salts.

Examples for salicylate derivatives include isopropylbenzyl salicylate, benzyl salicylate, butyl salicylate, octyl salicylate (NEO HELIOPAN OS), isooctyl salicylate or homomenthyl salicylate (homosalate, HELIOPAN);

Examples for triazone derivatives include octyl triazone (UVINUL T-150), dioctyl butamido triazone (UVASORB HEB).

Examples for triazol derivatives include benzotriazoles such as 2-(2-hydroxy-5-methylphanyl)benzotriazol, 2,2'-methylene-bis-(6-(2H-benzotriazole-2-yl)-4-(1,1,3,3,-tetramethylbutyl)-phenol (TINOSORB M) as well as triazols described in EP-A-893119

Examples for dibenzoylmethane derivatives include compounds such as 4-tert.butyl-4'-methoxydibenzoyl-methane (PARSOL® 1789), dimethoxydibenzoylmethane and isopropyldibenzoylmethane;

Examples for Amino substituted hydroxybenzophenones include compounds such as 2-(4-Diethylamino-2-hydroxy-benzoyl)-benzoic acid hexyl ester as described in the European Patent Publication EP 1046391.

Preferred residues A are
Benzophenone derivatives such as

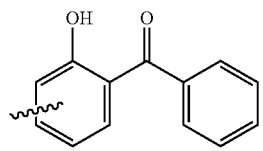

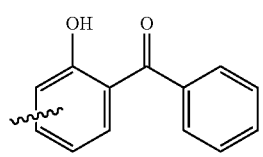

p-Aminobenzoic acid derivatives such as

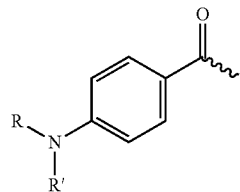

Benzoxazole derivatives such as

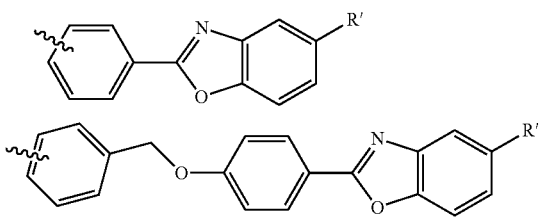

Camphor derivatives such as

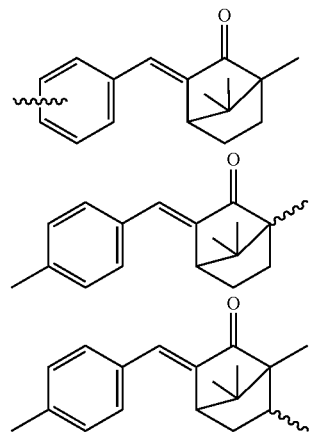

Cinnamic acid or benzalmalonate derivatives such as

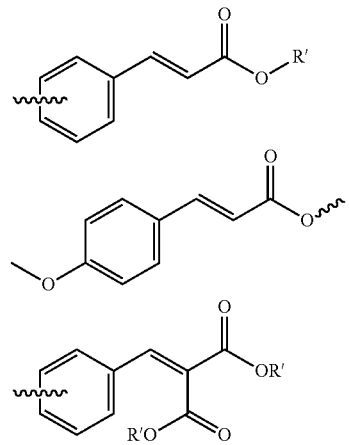

-continued

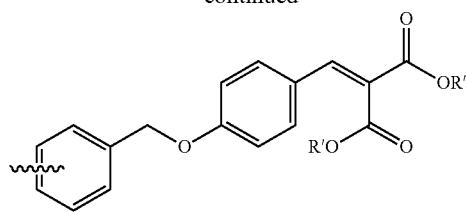

Benzimidazole derivatives such as

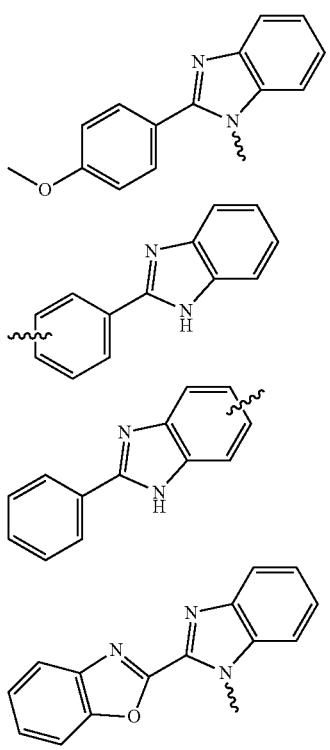

Octocrylene derivatives such as

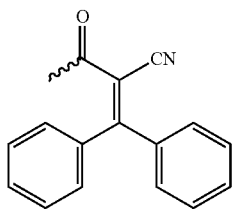

Benzotriazol derivatives such as

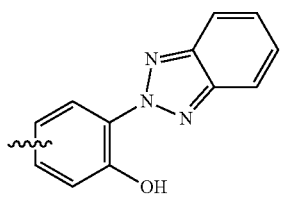

-continued

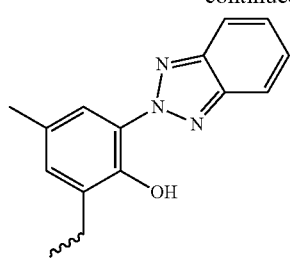

Dihydropyridine Derivatives such as

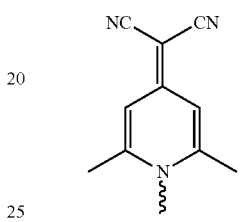

tert-Butyldibenzoylmethane derivatives such as

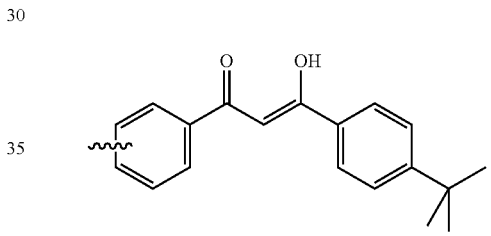

wherein R' is hydrogen, hydroxy, straight or branched chain $C_{1-20}$-alkyl, -alkoxy or $C_{2-20}$-alkenyl.

Preferably, the crosslinkable chromophore with UV filter activity is obtainable by reacting a silane molecule, e.g. of the formula $Si(R)_r(Q)_qS$, wherein R is a hydrolysable group as defined above, in particular an alkoxy group or an acyloxy group with 10 carbon atoms or less, Q is a non-hydrolysable group as defined above, in particular a $C_1$-$C_6$ alkyl group, e.g. methyl, S is a reactive group which can react with the chromophore, in particular a hydrogen atom, a group —$(CH_2)_o$—NCO, a group —$(CH_2)_o$—Cl or a group —$(CH_2)_o$—$NH_2$, r is 2 or 3, q is 0 or 1 and o is 1 to 6, such as

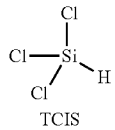

TCIS

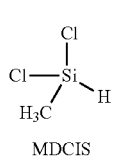

MDCIS

I

II

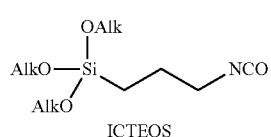
ICTEOS
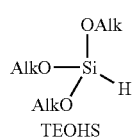
TEOHS
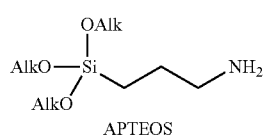
APTEOS
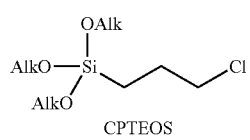
CPTEOS
wherein Alk is a $C_1$-$C_6$ alkyl group, preferably methyl or ethyl,
and a corresponding molecule with a chromophore selected e.g. from
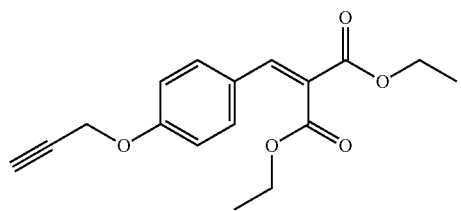
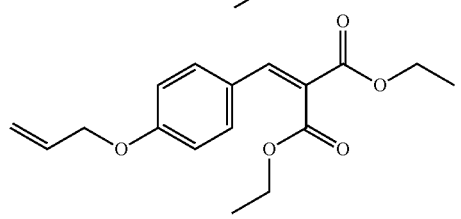
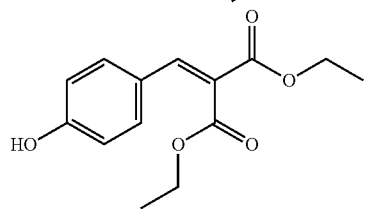
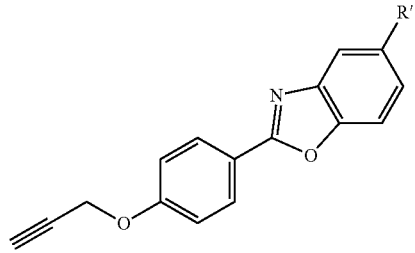
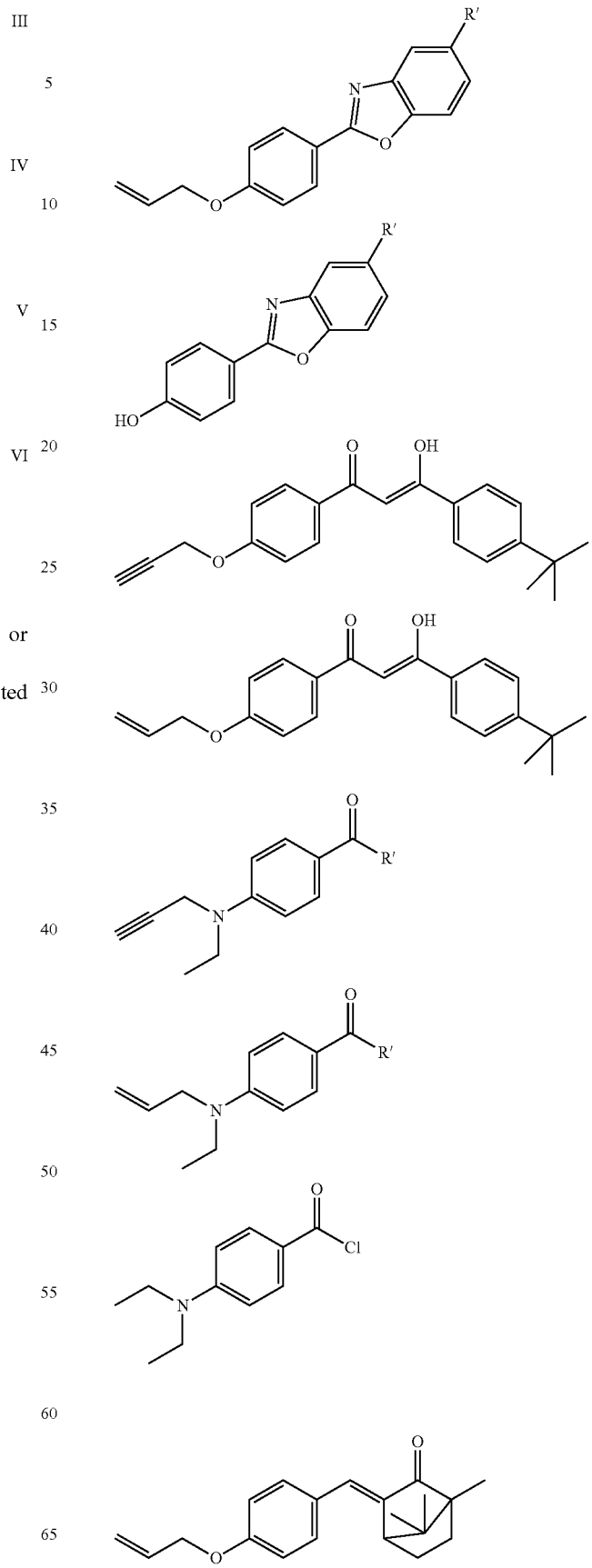

13
-continued
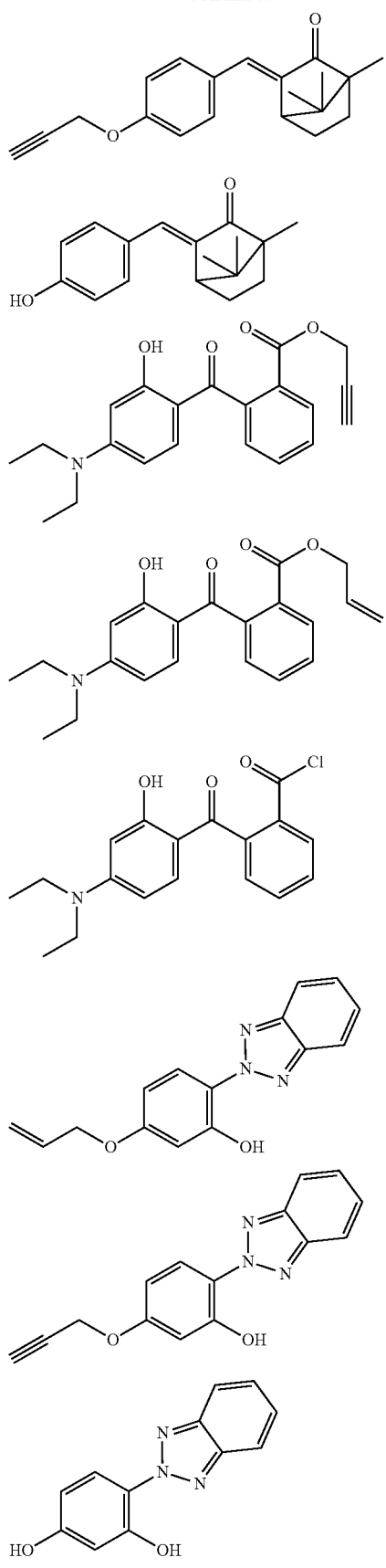
14
-continued
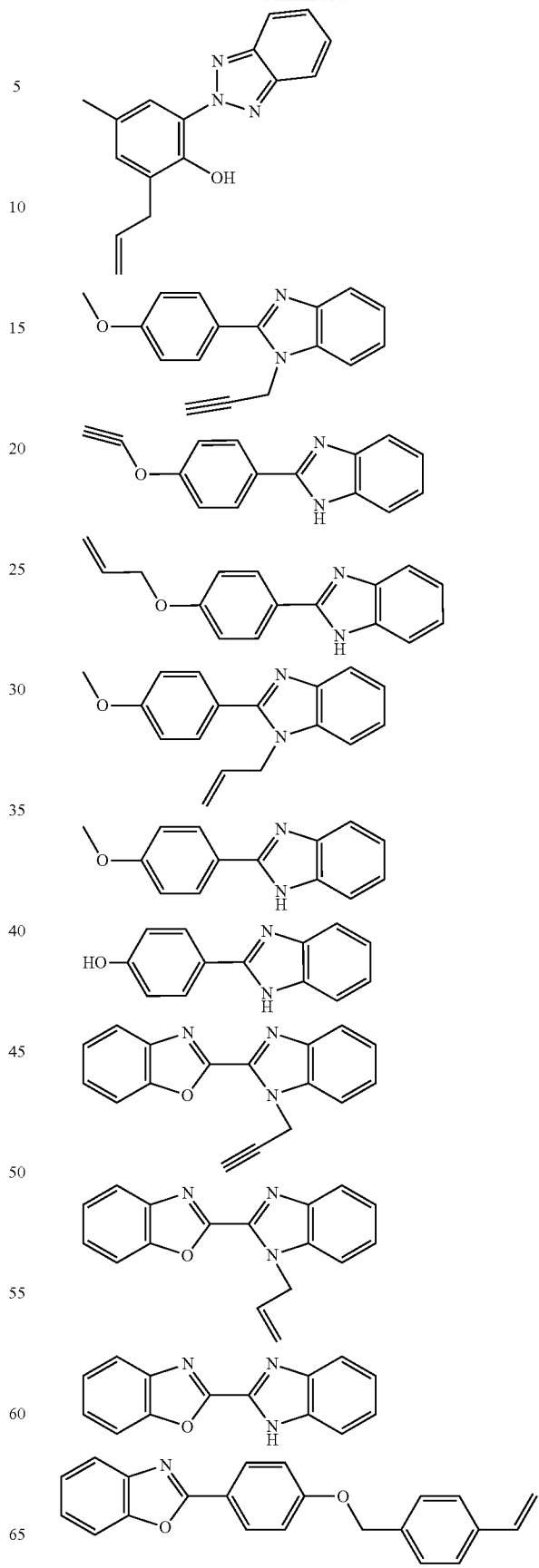

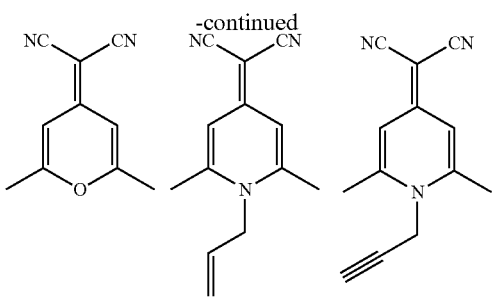

wherein R' is hydrogen, hydroxy, straight or branched chain $C_{1-20}$-alkyl, -alkoxy or $C_{2-20}$-alkenyl without being limited thereto.

It is also possible to prepare the crosslinkable chromophores by polymerizing one or more of the hydrolysable metal or semi-metal compounds, in particular the silane compounds mentioned above with each other or with other monomers such as the crosslinkable monomers with no UV filter activity defined below. In this case the crosslinkable chromophore is an oligomer which comprises one or more of the UV filter active moieties A. Usually such an oligomer is constituted from 50 monomer units or less, preferably from 20 monomer units or less, more preferably of 10 monomer units or less. Preferably such an oligomeric crosslinkable chromophore comprises 5 or less UV filter active moieties A, more preferably 3 or less, most preferably 1 UV filter active moiety A.

The crosslinkable chromophores with UV filter activity can be subjected to a crosslinking reaction per se or they can be subjected to a crosslinking reaction in the presence of crosslinkable monomers which do not have UV filter activity. Preferably, the crosslinkable chromophores with UV filter activity are subjected to a crosslinking reaction with crosslinkable monomers without UV filter activity, because this easily allows to adjust the amount of UV filter active moieties in the final microcapsules. Alternatively, it is also possible to adjust the amount of UV filter active moieties in the final microcapsules by crosslinking oligomers which have been prepared from monomers with UV filter activity and monomers with no UV filter activity as discussed above.

The crosslinkable monomers with no UV filter activity are preferably compounds of the formula $M(R)_n(Q)_q$, wherein M is a metallic or semi-metallic element such as silicon, titanium, zinc, aluminum or zirconium, preferably silicon, R is a hydrolysable substituent as defined above, preferably with not more than 10 carbon atoms, such as an alkoxide, an aryloxide, carboxylic ester, acyloxy group, diketonato group, hydrolysable aza group or a chlorine atom, preferably an alkoxide, an aryloxide or an acyloxy group, more preferably an alkoxide or an aryloxy group with 10 carbon atoms or less, in particular a $C_1$-$C_6$ alkoxide, most preferably methoxide or ethoxide, and n is an integer from 2 to 4, preferably 3 or 4, most preferably 4. Q is as defined above and q is 0 or 1, n+q=4.

Particularly preferred are crosslinkable monomers such as tetraethoxysilane (TEOS), tetramethoxysilane (TEMOS), methyltriethoxysilane (METEOS) or partially hydrolyzed and/or partially condensed polymers (oligomers) thereof or a mixture of the above. Suitable crosslinkable monomers are also disclosed e.g. in EP-A 216 278, and the other documents listed below which disclose details of the sol-gel process and which are incorporated herein by reference.

While the method for producing the microcapsules of the present invention is not particularly limited and all methods which are well known to a skilled person can principally be used, it is preferred to prepare the microcapsules by a sol-gel process, in particular if the crosslinkable monomers are metallic or semi-metallic compounds as defined above. The sol-gel process for producing microcapsules is well known to a skilled person. In the sol-gel method the crosslinkable monomers, preferably the silanes with and without UV filter activity as defined above are e.g. emulsified under high shear forces in an aqueous solution containing surfactants such as cetyltrimethylammonium chloride and the like and/or protective colloids such as PVP (polyvinylpyrolidon), PVA (polyvinyl alcohol) and the like that assist in stabilizing the emulsion. The obtained emulsion is mixed with an aqueous solution at a suitably selected pH value (basic, neutral or acidic) until spheres are formed. The spheres are then crosslinked under the formation of Si—O—Si bonds, e.g. by applying heat or changing the pH value, and a three-dimensional network is formed. The details of this process are well known, and it can be referred e.g. to WO 00/09652 and WO 00/72806, the content of which is included herein by reference insofar as it relates to the process for producing microcapsules. Other processes usable for the preparation of microcapsules via a sol-gel method are described e.g. in DE 41 24 588 and to EP 216 278. Regarding the sol-gel process it can also be referred e.g. to Colloid Polym. Sci. (2003) 281:19-26, DE-A 195 37 415.

Regarding the process steps and process conditions for preparing microcapsules by the sol-gel method it can also be referred to EP-A 216 278, WO 98/31333, U.S. Pat. No. 6,303, 149, EP-A 281 034 and EP-A 941 761, the content of which regarding the sol-gel process is incorporated herein by reference. Particularly preferred are the processes disclosed in EP-A 216 278 and U.S. Pat. No. 6,303,149, the content of which is incorporated herein by reference. A particularly preferred process is also disclosed in the examples.

The preparation of the microcapsules of the present invention by the sol-gel process has the advantage that the product obtained by this process is already in the form of a suspension containing about 1 to 80% solids consisting of sphere particles of 0.01-10 μm which can directly be used in the pharmaceutical compositions of the present invention. If advantageous, the product can also be dried and the product be used in the form of a dried powder.

Preferably, the microcapsules of the present invention have a particle size of 0.01-100 μm, more preferably of 0.01-10 μm. The amount of UV filter active moieties in the microcapsules is 10 to 80% w/w, more preferably 25 to 50% w/w. The above percentages relate to the weight of the UV filter active moieties A in the matrix material and are based on the total weight of the matrix material. The particle size is a mean particle size $d_v$ (0.5), if nothing else is stated.

It is possible that the microcapsules of the present invention contain two or more types of chromophores without the risk that there is an inactivation between the chromophore moieties, because the chromophore moieties are covalently bonded to the matrix material and therefore the risk of contact between the chromophore moieties is low. In a particular preferred embodiment of the present invention one or two kinds of crosslinkable chromophores are subjected to the crosslinking reaction, in particular the sol-gel process, most preferably together with at least one kind of crosslinkable monomer which does not have any UV filter activity. The microcapsules of the present invention thus preferably contain one or two different kinds of UV filter active moieties A as defined above, in a preferred embodiment only one kind of chromophore moieties as defined above in a ratio of 1:10 to 10:1, more preferably of 7:3 to 3:7, and in particular of about 1:1 to the crosslinkable monomer which does not have any UV filter activity. The ratio is based on a weight by weight basis.

The microcapsules of the present invention can be included within sunscreen compositions in manners well known to a skilled person. The sunscreen compositions are generally topical sunscreen compositions.

Surprisingly, the sunscreen compositions which are prepared with the microcapsules of the present invention have an excellent sunprotective factor which decrease only slightly if at all during storage or after being applied to the skin, even if two or more different UV filter active components are present which would usually inactivate each other.

For the preparation of the topical sunscreen compositions, especially preparations for dermatological and/or cosmetic use, such as skin protection and sunscreen formulations for everyday cosmetics microcapsules carrying a covalent bonded UV-filter can be incorporated in auxiliary agents, e.g. a cosmetic base, which are conventionally used for such formulations. Where convenient, other conventional UV-A and/or UV-B and/ or broad spectrum screening agents may also be added. The combination of UV screens may show a synergistic effect. The amount of the microcapsules carrying a covalently bonded UV-filter and other known UV-screens is not critical. Suitable amounts of the microcapsules carrying a covalently bonded UV-filter are about 10 to about 50% by weight (depending on the payload and volume fraction of the microcapsules) and about 0.5-12% by weight of at least one additional, hydrophilic and/or lipophilic UV-A or UV-B or broad spectrum screening agent. These additional screening agents are advantageously selected from among the compounds listed below without being limited thereto:

Examples of UV B or broad spectrum screening agents, i.e. substances having absorption maximums between about 290 and 340 nm, which come into consideration for combination with the compounds of the present invention are for example the following organic and inorganic compounds:

Acrylates such as 2-ethylhexyl 2-cyano-3,3-diphenylacrylate (octocrylene, PARSOL® 340), ethyl 2-cyano-3,3-diphenylacrylate and the like;

Camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like;

Cinnamate derivatives such as octyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes;

p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate, Benzophenones such as benzophenone-3, benzophenone-4, 2,2',4,4'-tetrahydroxy-benzophenone, 2,2'-dihydroxy-4,4'-dimethoxybenzophenone and the like;

Esters of Benzalmalonic acid such as di-(2-ethylhexyl) 4-methoxybenzalmalonate;

Esters of 2-(4-ethoxy-anilinomethylene)propandioic acid such as 2-(4-ethoxy anilinomethylene)propandioic acid diethyl ester as described in the European Patent Publication EP 0 895 776;

Organosiloxane compounds containing benzmalonate groups as described in the European Patent Publications EP 0358584 B1, EP 0538431 B1 and EP 0709080 A1;

Drometrizole trisiloxane (Mexoryl XL);

Pigments such as microparticulated $TiO_2$, and the like. The term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art.

Imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like.

Salicylate derivatives such as isopropylbenzyl salicylate, benzyl salicylate, butyl salicylate, octyl salicylate (NEO HELIOPAN OS), isooctyl salicylate or homomenthyl salicylate (homosalate, HELIOPAN) and the like;

Triazine derivatives such as octyl triazone (UVINUL T-150), dioctyl butamido triazone (UVASORB HEB), bis ethoxyphenol methoxyphenyl triazine (Tinosorb S) and the like.

Examples of broad spectrum or UV A screening agents i.e. substances having absorption maximums between about 320 and 400 nm, which come into consideration for combination with the compounds of the present invention are for example the following organic and inorganic compounds:

Dibenzoylmethane derivatives such as 4-tert.butyl-4'-methoxydibenzoylmethane (PARSOL® 1789), dimethoxydibenzoylmethane, isopropyldibenzoylmethane and the like;

Benzotriazole derivatives such as 2,2'-methylene-bis-(6-(2H-benzotriazole-2-yl)-4-(1,1,3,3,-tetramethylbutyl)-phenol (TINOSORB M) and the like;

phenylene-1,4-bis-benzimidazolsulfonic acids or salts such as 2,2-(1,4-phenylene)bis-(1H-benzimidazol-4,6-disulfonic acid) (Neoheliopan AP);

amino substituted hydroxybenzophenones such as 2-(4-Diethylamino-2-hydroxy-benzoyl)-benzoic acid hexylester as described in the European Patent Publication EP 1046391

Pigments such as microparticulated ZnO or $TiO_2$ and the like. The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g., 3,3-Diphenylacrylate derivatives as described in the European Patent Publications EP 0 514 491 B1 and EP 0 780 119 A1;

Benzylidene camphor derivatives as described in the U.S. Pat. No. 5,605,680;

Organosiloxanes containing benzmalonate groups as described in the European Patent Publications EP 0358584 B1, EP 0538431 B1 and EP 0709080 A1.

The compositions of the invention can also contain usual cosmetic adjuvants and additives, such as preservatives/antioxidants, fatty substances/oils, water, organic solvents, silicones, thickeners, softeners, emulsifiers, additional sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, in particular those suited for providing an additional photoprotective effect by physically blocking out ultraviolet radiation, or any other ingredients usually formulated into cosmetics, in particular for the production of sunscreen/antisun compositions. The necessary amounts of the cosmetic and dermatological adjuvants and additives can, based on the desired product, easily be chosen by a skilled artisan in this field and will be illustrated in the examples, without being limited hereto.

An additional amount of antioxidants/preservatives is generally preferred. Based on the invention all known antioxidants usually formulated into cosmetics can be used. Especially preferred are antioxidants chosen from the group consisting of amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinsulfoximine, buthioninsulfone, penta-, hexa-, heptathioninsulfoximine) in very low compatible doses (e.g. pmol bis µmol/kg), additionally (metal)-chelators (such as α-hydroxyfatty acids, palmic-, phytinic acid, lactoferrin), β-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, ascorbylacetate), tocopherole and derivates (such as vitamin-E-acetate), mixtures of nat. vitamin E, vitamin A and derivatives (vitamin-A-palmitate and -acetate) as well as coniferylbenzoat, rutinic acid and derivatives, α-glycosylrutin, ferulic acid, furfurylidenglucitol, carnosin, butylhydroxytoluene, butylhydroxyanisole, trihydroxybutyrophenone, urea and its derivatives, mannose and derivatives, zinc and derivatives (e.g. ZnO, $ZnSO_4$), Selen and derivatives (e.g. selenomethionin), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount about 0.01 wt. % to about 10 wt. % of the total weight of the composition of the present invention. Preferably, one or more preservatives/antioxidants are present in an amount about 0.1 wt. % to about 1 wt. %.

Typically formulations also contain surface active ingredients like emulsifiers, solubilizers and the like. An emulsifier enables two or more immiscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount about 0.01 wt. % to about 20 wt. % of the total weight of the composition of the present invention. Preferably, about 0.1 wt. % to about 10 wt. % of emulsifiers are used.

The lipid phase can advantageously be chosen from:
mineral oils and mineral waxes;
oils such as triglycerides of caprinic acid or caprylic acid, preferable castor oil;
oils or waxes and other natural or synthetic oils, in an preferred embodiment esters of fatty acids with alcohols e.g. isopropanol, propyleneglycol, glycerine or esters of fatty alcohols with carbonic acids or fatty acids;
alkylbenzoates; and/or
silicone oils such as dimethylpolysiloxane, diethylpolysiloxane, diphenylpolysiloxane, cyclomethicones and mixtures thereof.

Exemplary fatty substances which can be incorporated in the oil phase of the emulsion, microemulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaureate, n-decyloleat, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for use in the formulation of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbonatoms whereas the fatty acid triglycerides are preferably chosen from synthetic, half synthetic or natural oils (e.g.

cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicone (octamethylcyclotetrasiloxane; cetyldimethicone, hexamethylcyclotrisiloxane, polydimethylsiloxane, poly(methylphenylsiloxane) and mixtures thereof.

Other fatty components which can advantageously be incorporated in formulations of the present invention are isoeikosane; neopentylglycoldiheptanoate; propyleneglycoldicaprylate/dicaprate; caprylic/capric/diglycerylsuccinate; butylenglycol caprylat/caprat; $C_{12-13}$-alkyllactate; di-$C_{12-13}$ alkyltartrate; triisostearin; dipentaerythrityl hexacaprylat/hexacaprate; propylenglycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate. The oily phase of the formulation of the present invention can also contain natural vegetable or animal waxes such as bee wax, china wax, bumblebee wax and other waxes of insects as well as shea butter and cocoa butter.

A moisturizing agent may be incorporated into a composition of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimeticone, cyclometicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (ENJAY), diisopropyl adipate, hydroxybenzoate esters, benzoic acid esters of $C_{9-15}$-alcohols, isononyl iso-nonanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 wt. % to about 20 wt. % of the total weight of the composition. The preferred amount of emollient is about 2 wt. % to about 15 wt. %, and most preferably about 4 wt. % to about 10 wt. %.

Moisturizers that bind water, thereby retaining it on the skin surface are called humectants. Suitable humectants can be incorporated into a composition of the present invention such as glycerin, polypropylene glycol, polyethylene glycol, lactic acid, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a composition of the present invention, preferably about 1 wt. % to about 5 wt. %.

The aqueous phase of the compositions of the present invention can contain the usual cosmetic additives such as alcohols, especially lower alcohols, preferably ethanol and/or isopropanol, low diols or polyols and their ethers, preferably propyleneglycol, glycerine, ethyleneglycol, ethyleneglycol monoethyl- or monobutylether, propyleneglycol monomethyl-or -monoethyl- or-monobutylether, diethyleneglycol monomethyl-or monoethylether and analogue products, polymers, foam stabilizers; electrolytes and especially one or more thickeners. Thickeners that may be used in formulations of the present invention to assist in making the consistency of a product suitable include carbomer, siliciumdioxide, magnesium and/ or aluminum silicates, beeswax, stearic acid, stearyl alcohol polysaccharides and their derivatives such as xanthan gum, hydroxypropyl cellulose, polyacrylamides, acrylate crosspolymers preferably a carbomer, such as carbopole® of type 980, 981, 1382, 2984, 5984 alone or mixtures thereof. Suitable neutralizing agents which may be included in the composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt. % to about 8 wt. % in the composition of the present invention, preferably, 1 wt. % to about 5 wt. %.

The addition of electrolytes into the composition of the present invention may be necessary to change the behavior of a hydrophobic emulsifier. Thus, the emulsions/microemulsions of this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the composition of the present invention.

The cosmetic compositions of the invention are useful as compositions for photoprotecting the human epidermis or hair against the damaging effect of ultraviolet irradiation, as sunscreen compositions. Such compositions can, in particular, be provided in the form of a lotion, a thickened lotion, a gel, a cream, a milk, an ointment, a powder or a solid tube stick and can be optionally be packaged as an aerosol and can be provided in the form of a mousse, foam or a spray. When the cosmetic composition according to the invention are provided for protecting the human epidermis against UV radiation or as sunscreen composition, they can be in the form of a suspension or dispersion in solvents or fatty substances, or alternatively in the form of an emulsion or microemulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

The following examples are provided to further illustrate the processes and compositions of the present invention. These examples are illustrative only and are not intended to limit the scope of the invention in any way.

EXAMPLES

Example 1 a) 4-(2-Benzoxazolyl)-phenol

A 250 ml three necked reaction flask, equipped with a reflux condenser combined with a water separator and an oil bath with a magnetic stirrer was charged with 16.4 g (150 mmol) of 2-aminophenol (Fluka), 20.8 g (150 mmol) of 4-hydroxy-benzoic acid and 1.2 g of boric acid in 150 ml of 1,2-dichlorobenzene. After 18 hours of reflux 5 ml of water were separated. On tlc (hexane/ethylacetate=3:2) no starting material could be observed. The reaction mixture was cooled and diluted with hexane. Crystals were formed, which were filtered off, washed with hexane and dried at 60° C. in a vacuum to yield 31.3 g (99%) of the product. M.p. 242-245° C. UV (ethanol) 306 nm (31'831).

b) 2-(4-allyloxyphenyl)-benzoxazole

A 500 ml round bottom flask, equipped with a reflux condenser and an oil bath with a magnetic stirrer was charged with 13.94 g of the above 4-(2-benzoxazolyl)-phenol, 9.7 g of allyl bromide and 17.5 g of anhydrous $Na_2CO_3$ in 300 ml of 1-methyl-2-pyrrolidone. A trace of KJ was added. After 5 h hour at 110° C. no starting material could be observed on tlc. The reaction mixture was diluted with ethylacetate and washed with 1n NaOH, water and NaCl solution, dried with $Na_2SO_4$, concentrated and recrystallised from hexene to yield 14.3 g (86%) of 2-(4-prop-2-enyloxy-phenyl)-benzoxazole. M.p. 95-96° C., UV (ethanol) 308 nm (26'184).

c) (4-(3-(triethoxysily)propoxyl)phenyl)-benzoxazole

A 250 ml round bottom flask, equipped with a reflux condenser and an oil bath with a magnetic stirrer was charged with 4.0 g (22 mmol) triethoxysilane and 5.0 g (20 mmol) of the above 2-(4-allyloxyphenyl)-benzoxazole in 100 ml of toluene under nitrogen atmosphere. The reaction mixture was heated to 70° C. and a catalytic amount of divinyl-tetramethyl disiloxane platinum complex was added. After the reaction mixture was heated for 2 hours, another 1.8 g (11 mmol) triethoxysilane were added and the reaction mixture was stirred over night. The product solution was evaporated, diluted with toluene and filtrated over Celite to yield 8 g (96%) of crude (4-(3-(triethoxysilyl)propyloxy])phenyl)-benzoxazole. UV (ethanol) 308 nm (23'468).

Example 2

(4-(3-(triethoxysilyl)propyl]amino]carbonyl]oxy]) phenyl)-benzoxazole

Into a stirred solution of 0.5 g (2.4 mmol) of 4-(2-Benzoxazolyl)-phenol prepared as described in example 1 of in 10 ml of tetrahydrofurane and a few drops of dibutyltindilaurate catalyst, was added 0.6 g (2.52 mmol) of ICTEOS under nitrogen atmosphere. The mixture was stirred for 18 h at 30° C. After removal of the solvent, the product was precipitated with hexane, filtrated and dried to yield 0.99 g (90%) of (4-(3-(triethoxysilyl)propyl]-amino]carbonyl]oxy])phenyl)-benzoxazole. M.p. 141-142° C.; UV (ethanol) 304 nm (24'630).

Example 3

2-[[4-[3-(trimethoxysilyl)propoxy]benzylidene]-malonic acid diethyl ester

A 250 ml round bottom flask, equipped with a reflux condenser and an oil bath with a magnetic stirrer was charged with 10.0 g (82 mmol) trimethoxysilane and 5.0 g (16.4 mmol) of 2-[[4-(prop-2-enyloxy)benzylidene]-malonic acid diethyl ester in 100 ml of toluene under nitrogen atmosphere. The reaction mixture was heated to 70° C. and a catalytic amount of divinyl-tetramethyl disiloxane platinum complex was added. After the reaction mixture was heated for 2 hours, the solution was concentrates and filtrated over Celite to yield 6.2 g (88%) of crude 2-[[4-[3-(trimethoxysilyl)propoxy]benzylidene]-malonic acid diethyl ester as yellow oil. UV (ethanol) 312 nm (24'793).

Example 4

2-[[4-[2-(trimethoxysilyl)prop2-enyloxy]benzylidene]-malonic acid diethyl ester

A 250 ml round bottom flask, equipped with a reflux condenser and an oil bath with a magnetic stirrer was charged with 2.2 g (18 mmol) trimethoxysilane and 5.0 g (16.5 mmol) of propanedioic acid, [[4-(2-propynyloxy)phenyl]methylene]diethyl ester in 100 ml of toluene under nitrogen atmosphere. The reaction mixture was heated to 70° C. and a catalytic amount of divinyl-tetramethyl disiloxane platinum complex was added. After the reaction mixture was heated for 2 hours, the solution was concentrated and filtrated over Celite to yield 7.1 g (100%) of 2-[[4-[2-(trimethoxysilyl)prop-2enyloxy]benzylidene]-malonic acid diethyl ester as yellow oil. UV (ethanol) 312 nm (24'623).

Example 5

2-[[4-[2-(triethoxysilyl)prop2-enyloxy]benzylidene]-malonic acid diethyl ester

A 1000 ml round bottom flask, equipped with a reflux condenser and an oil bath with a magnetic stirrer was charged with 72 g (0.44 mol) triethoxysilane and 120 g (0.4 mol) of propanedioic acid [[4-(2-propynyloxy)phenyl]methylene]diethyl ester in 500 ml of toluene under nitrogen atmosphere. The reaction mixture was heated to 70° C. and a catalytic amount of divinyl-tetramethyl disiloxane platinum complex was added. After the reaction mixture was heated for 20 hours, another 6.6 g (0.04 mol) triethoxysilane are added and the mixture was stirred for an additional 4 h. Afterwards, the solution was concentrated, dissolved in dichloromethane and washed twice with water. After drying over NaSO4 the organic phase is concentrated and purified via column chromatography (hexane/EtOAc) yielding 35.4 g (19%) of 2-[[4-[2-(triethoxysilyl)prop2-enyloxy]benzylidene]-malonic acid diethyl ester as yellow oil. UV (ethanol) 314 nm (23'926).

Example 6

1.5 g of 2-[[4-[2-(triethoxysilyl)prop2-enyloxy]benzylidene]-malonic acid diethyl ester prepared as described in example 5 was dissolved in 7.5 g Tetraethoxysilane. The organic phase was emulsified in 50 g of an aqueous solution containing 1% cetyltrimethylammonium chloride (CETAC) under high shear forces using an Ultra Tourrax T-25 basic at 17500 rpm. This emulsion was then poured into a 250 ml round flask containing 50 g of aqueous NaOH solution at pH 11 at 60° C. and stirred for 3 days. The final suspension contained microcapsules loaded with 20% w/w chromophore and a particle size $d_v(0.5)=5$ µm. The obtained powder was incorporated into an emulsion as described in Example 7 yielding an in vitro SPF value of 5.

Example 7

W/O Sunscreen Emulsion

|   |   | % |
|---|---|---|
| A) | Brij 721 | 2.00 |
|   | Brij 72 | 2.00 |
|   | Cetyl Alkohol | 2.00 |
|   | Stearyl Alkohol (Lanette 18) | 1.00 |
|   | Lanette 22 | 1.00 |
|   | Myritol 318 | 11.20 |
|   | Tegosoft TN | 2.00 |
|   | Arlamol HD (Isohexadecane) | 3.00 |
|   | BHT | 0.05 |
|   | Phenonip | 1.00 |
| B) | Aqua | 58.50 |
|   | Glycerin | 5.00 |
|   | Edeta BD | 0.10 |
| C) | KOH 10% | 0.15 |
| D) | Sepigel 305 | 1.00 |
| E) | Microcapsules of example 6 | 10.00 |
|   |   | 100.00 |

Heat part A) and B) to 85° C. while stirring. Add part B) to A) under agitation. Cool to about 45° C. while stirring Then add part C). Add part D) at 40° C. Cool to ambient temperature while stirring. Add part E). Homogenize again to achieve a small particle size.

Example 8

O/W Sun Milk with Pigments

|   | Ingredients | INCI Nomenclature | % w/w |
|---|---|---|---|
| A) | PARSOL SLX | Polysilicone-15 | 6.00 |
|   | Neo Heliopan AP |   | 3.00 |
|   | Tinosorb S | Hydrogenated Cocoglycerides | 3.00 |
|   | Lanette O | Cetearyl Alcohol | 2.00 |
|   | Myritol 318 | Caprylic/capric Triglyceride | 6.00 |
|   | Mineral oil | Mineral oil | 2.00 |
|   | Vitamin E acetate | Tocopheryl Acetate | 1.00 |
|   | Prisorine 3515 | Isostearyl Alcohol | 4.00 |
| B) | Edeta BD | Disodium EDTA | 0.10 |
|   | Phenonip | Phenoxyethanol & Methylparaben & Ethylparaben & Propylparaben & Butylparaben | 0.60 |
|   | Amphisol K | Potassium Cetyl Phosphate | 2.00 |
|   | Water deionized | Aqua | ad 100 |
|   | 1,2-Propylen Glycol | Propylene Glycol | 5.00 |
|   | Carbopol 981 | Carbomer | 0.30 |
|   | Tinosorb M | Methylene Bis-Benzotriazolyl Tetramethylbutylphenol | 6.00 |
|   | KOH 10% solution | Potassium Hydroxyde | 2.10 |
| C) | Microcapsules of the invention |   | 1-50% |

Procedure:

Heat part A) and B) to 85° C. while stirring. When homogeneous, add part B) to A) under agitation. Cool to ambient temperature while stirring and add part C). Homogenize to achieve a small particle size.

Example 9

Sun Milk Waterproofed

|   | Ingredients | INCI Nomenclature | % w/w |
|---|---|---|---|
| A) | PARSOL SLX | Polysilicone-15 | 6.00 |
|   | PARSOL 1789 | Butyl Methoxydibenzoylmethane | 2.00 |

-continued

|   | Ingredients | INCI Nomenclature | % w/w |
|---|---|---|---|
|   | PARSOL 5000 | 4-Methylbenzylidene Camphor | 4.00 |
|   | Uvinul T 150 | Ethylhexyltriazone | 2.00 |
|   | Silicone DC 200/ 350 cs | Dimethicone | 1.00 |
|   | Lanette O | Cetearyl Alcohol | 2.00 |
|   | Softisan 100 | Hydrogenated Coco-Glycerides | 3.00 |
|   | Tegosoft TN | C12-15 Alkyl Benzoate | 6.00 |
|   | Cetiol B | Dibutyl Adipate | 7.00 |
|   | Vitamin E acetate | Tocopheryl Acetate | 2.00 |
|   | BHT | BHT | 0.05 |
|   | Edeta BD | Disodium EDTA | 0.10 |
|   | Phenonip | Phenoxyethanol & Methylparaben & Ethylparaben & Propylparaben & Butylparaben | 0.60 |
|   | Amphisol | Cetyl Phosphate DEA | 2.00 |
| B) | Water deionized | Aqua | ad 100 |
|   | Propylene Glycol | Propylene Glycol | 5.00 |
|   | Carbopol 980 | Carbomer | 0.30 |
|   | KOH (10% sol.) | Potassium Hydroxide | 1.50 |
| C) | Microcapsules of the invention |   | 1-50% |

Procedure:

Heat part A) and B) to 85° C. while stirring. When homogeneous, add part B) to A) under agitation. Cool to ambient temperature while stirring and add part C). Homogenize to achieve a small particle size.

Example 10

Sun Milk for Babies and Children

|   | Ingredients | INCI Nomenclature | % w/w |
|---|---|---|---|
| A) | Titanium Dioxide | Titanium Dioxide microfine | 4.00 |
|   | Tegosoft TN | C12-15 Alkyl Benzoate | 5.00 |
|   | Silicone 2503 Cosmetic Wax | Stearyl Dimethicone | 2.00 |
|   | Cetyl Alcohol | Cetyl Alcohol | 1.00 |
|   | Butylated Hydroxytoluene | BHT | 0.05 |
|   | Estol GMM 3650 | Glyceryl Myristate | 4.00 |
|   | Edeta BD | Disodium EDTA | 0.10 |
|   | Phenonip | Phenoxyethanol & Methylparaben & Ethylparaben & Propylparaben & Butylparaben | 0.60 |
|   | Amphisol A | Cetyl Phosphate | 2.00 |
| B) | Water deionized | Aqua | ad 100 |
|   | Carbopol 980 | Carbomer | 0.6 |
|   | Glycerine | Glycerine | 3.00 |
|   | KOH sol. 10% | Potassium Hydroxide | 2.4 |
| C) | Microcapsules of the invention |   | 1-50% |

Procedure:

Heat part A) and B) to 85° C. while stirring. When homogeneous, add part B) to A) under agitation. Cool to ambient temperature while stirring and add part C). Homogenize to achieve a small particle size.

Example 11

High Protective Sun Milk

|   | Ingredients | INCI Nomenclature | % w/w |
|---|---|---|---|
| A) | PARSOL SLX | Polysilicone-15 | 6.00 |
|   | PARSOL 1789 | Butyl Methoxydibenzoylmethane | 2.00 |
|   | PARSOL 5000 | 4-Methylbenzylidene Camphor | 4.00 |
|   | Uvinul T 150 |   | 2.00 |
|   | Silicone DC 200/ 350 cs | Dimethicone | 1.00 |
|   | Lanette O | Cetearyl Alcohol | 2.00 |
|   | Softisan 100 | Hydrogenated Coco-Glycerides | 3.00 |
|   | Tegosoft TN | C12-15 Alkyl Benzoate | 6.00 |
|   | Cetiol B | Dibutyl Adipate | 7.00 |
|   | Vitamin E acetate | Tocopheryl Acetate | 2.00 |
|   | BHT | BHT | 0.05 |
|   | Edeta BD | Disodium EDTA | 0.10 |
|   | Phenonip | Phenoxyethanol & Methylparaben & Ethylparaben & Propylparaben & Butylparaben | 0.60 |
|   | Amphisol K | Potassium Cetyl Phosphate | 2.00 |
| B) | Water deionized | Aqua | ad 100 |
|   | Propylene Glycol | Propylene Glycol | 5.00 |
|   | Carbopol 980 | Carbomer | 0.30 |
|   | KOH (10% sol.) | Potassium Hydroxide | 1.50 |
| C) | Microcapsules of the invention |   | 1-50% |
| D) | Perfume | Perfume | q.s. |

Procedure:

Heat part A) and B) to 85° C. while stirring. When homogeneous, add part B) to A) under agitation. Cool to ambient temperature while stirring and add part C) and D). Homogenize to achieve a small particle size.

Example 12

Water-free Sun Gel

|   | Ingredients | INCI Nomenclature | % w/w |
|---|---|---|---|
| A) | PARSOL MCX | Ethylhexyl Methoxycinnamate | 6.00 |
|   | PARSOL 1789 | Butyl Methoxydibenzoylmethane | 4.00 |
|   | PARSOL 5000 | 4-Methylbenzylidene Camphor | 4.00 |
|   | Uvasorb HEB | Diethylhexyl Butamido Triazone | 1.50 |
|   | Uvinul A plus |   | 2.00 |
|   | Vitamin E acetate | Tocopheryl Acetate | 1.50 |
|   | Tegosoft TN | C12-15 Alkyl Benzoate | 9.00 |
|   | Elefac I-205 | Ethylhexyldodecyl Neopentanoate | 2.00 |
|   | Alcohol | Alcohol | ad 100 |
|   | Isopropyl Alcohol | Isopropyl Alcohol | 20.00 |
| B) | Klucel MF | Hydroxypropylcellulose | 2.00 |
| C) | Microcapsules of the invention |   | 1-50% |
| D) | perfume |   | q.s. |

Procedure:

Mix part A) and B) while stirring. When homogeneous, add part C) and D) under agitation.

Example 13

Sun Gel

|   | Ingredients | INCI Nomenclature | % w/w |
|---|---|---|---|
| A) | Pemulen TR-2 | Acrylates/C10-30 Alky Acrylate Crosspolymer | 0.60 |

-continued

|   | Ingredients | INCI Nomenclature | % w/w |
|---|---|---|---|
|   | Phenonip | Phenoxyethanol & Methylparaben & Ethylparaben & Propylparaben & Butylparaben | 0.60 |
|   | Edeta BD | Disodium EDTA | 0.1 |
|   | Aqua | Aqua | ad 100 |
| B) | PARSOL 1789 | Butyl Methoxydibenzoylmethane | 4.00 |
|   | PARSOL 340 | Octocrylene | 3.00 |
|   | Tegosoft TN | C12-15 Alkyl Benzoate | 15.00 |
|   | Antaron V-216 | PVP/Hexadecene Copolymer | 1.00 |
|   | Vitamin E acetate | Tocopheryl Acetate | 0.50 |
|   | Uvinul TiO2 | Titanium Dioxide | 5.00 |
|   | Butylated Hydroxytoluene | BHT | 0.05 |
|   | Cremophor RH 410 | PEG-40 Hydrogenated Castor Oil | 0.50 |
|   | Tris Amino | Trometamine | 0.50 |
| C) | Microcapsules of the invention |   | 1-50% |
| D) | Perfume | Perfume | q.s. |

Procedure:

Heat part A) and B) to 85° C. while stirring. When homogeneous, add part B) to A) under agitation. Cool to ambient temperature while stirring and add part C) and D). Homogenize to achieve a small particle size.

Example 14

High Protection WO Sun Milk

|   | Ingredients | INCI Nomenclature | % w/w |
|---|---|---|---|
| A) | PARSOL 1789 | Butyl Methoxydibenzoylmethane | 2.00 |
|   | PARSOL 5000 | 4-Methylbenzylidene Camphor | 4.00 |
|   | Uvinul T 150 | Ethylhexyl Triazone | 2.00 |
|   | Uvinul TiO2 | Titanium Dioxide and Trimethoxycaprylylsilane | 5.00 |
|   | Arlacel P 135 | PEG-30 Dipolyhydroxystearate | 2.00 |
|   | Tegosoft TN | C12-15 Alkyl Benzoate | 5.00 |
|   | Cosmacol EMI | Di-C12-13 Alkyl Malate | 6.00 |
|   | Miglyol 840 | Propylene Glycol Dicaprylate/Dicaprate | 6.00 |
|   | Butylated Hydroxytoluene | BHT | 0.05 |
|   | Phenonip | Phenoxyethanol & Methylparaben & Ethylparaben & Propylparaben & Butylparaben | 0.60 |
| B) | Deionized water | Aqua | ad 100 |
|   | Glycerin | Glycerin | 5.00 |
|   | Edeta | Disodium EDTA | 0.1 |
|   | NaCl | Sodium Chloride | 0.30 |
| C) | PARSOL HS | Phenylbenzyimidazole Sulphonic Acid | 4.00 |
|   | Water | Aqua | 20.00 |
|   | Triethanolamine 99%. | Triethanolamine | 2.50 |
| D) | Microcapsules of the invention |   | 1-50% |
| E) | Perfume |   | q.s. |

Procedure:

Heat part A), B) and C) to 85° C. while stirring. When homogeneous, add part B) and C) to A) under agitation. Cool to ambient temperature while stirring and add part D) and E). Homogenize to achieve a small particle size.

Example 15

W/O Milk with Pigments

| | Ingredients | INCI Nomenclature | % w/w |
|---|---|---|---|
| A) | Cremophor WO 7 | PEG-7 Hydrogenated Castor Oil | 6.00 |
| | Elfacos ST 9 | PEG-45/Dodecyl Glycol Copolymer | 2.00 |
| | PARSOL 1789 | Butyl Methoxydibenzoylmethane | 3.00 |
| | Tinosorb S | | 5.00 |
| | PARSOL 5000 | 4-Methylbenzylidene Camphor | 4.00 |
| | Uvinul TiO2 | Titanium Dioxide | 2.00 |
| | microfine ZnO | Zinc Oxide | 2.00 |
| | Microcrystalline wax | Microcrystalline Wax | 2.00 |
| | Miglyol 812 | Caprylic/capric Triglyceride | 5.00 |
| | Vitamin E acetate | Tocopheryl Acetate | 1.00 |
| | Jojoba oil | *Simmondsia Chinensis* Seed Oil | 5.00 |
| | Edeta BD | Disodium EDTA | 0.10 |
| | Butylated Hydroxytoluene | BHT | 0.05 |
| | Phenonip | Phenoxyethanol & Methylparaben & Ethylparaben & Propylparaben & Butylparaben | 0.60 |
| B) | Water deionized | Aqua | ad 100 |
| | Glycerin | Glycerin | 5.00 |
| C) | Neo Heliopan AP | | 2.00 |
| | Water deionized | Aqua | 20.00 |
| | KOH 10% solution | Potassium Hydroxide | 4.00 |
| D) | Microcapsules of the invention | | 1-50% |
| E) | Perfume | Perfume | q.s. |

Procedure:

Heat part A), B) and C) to 85° C. while stirring. When homogeneous, add part B) and C) to A) under agitation. Cool to ambient temperature while stirring and add part D) and E). Homogenize to achieve a small particle size.

Example 16

Protective Day Cream with Vitamin C

| | Ingredients | INCI Nomenclature | % w/w |
|---|---|---|---|
| A) | PARSOL SLX | Polysilicone-15 | 4.00 |
| | PARSOL 1789 | Butyl Methoxydibenzoylmethane | 1.50 |
| | Glyceryl Myristate | Glyceryl Myristate | 2.00 |
| | Cetyl Alcohol | Cetyl Alcohol | 0.50 |
| | Myritol 318 | Caprylic/Capric Triglyceride | 5.00 |
| | Crodamol DA | Diisopropyl Adipate | 5.00 |
| | Vitamin E acetate | Tocopheryl Acetate | 2.00 |
| | Butylated Hydroxytoluene | BHT | 0.05 |
| | Phenonip | Phenoxyethanol & Methylparaben & Ethylparaben & Propylparaben & Butylparaben | 0.60 |
| | Edeta BD | Disodium EDTA | 0.10 |
| | Amphisol K | Potassium Cetyl Phosphate | 2.00 |
| B) | Water deionized | Aqua | ad 100 |
| | 1,2-Propylene Glycol | Propylene Glycol | 2.00 |
| | D-Panthenol 75 L | Panthenol | 2.00 |
| | Ethanol | Ethanol | 5.00 |
| | Allantoin | Allantoin | 0.20 |
| | Carbopol ETD 2001 | Carbomer | 0.30 |
| | KOH 10% sol. | Potassium Hydroxide | 1.50 |
| C) | Water | Aqua | 10.00 |
| | Stay-C 50 | Sodium Ascorbyl Phosphate | 0.50 |
| D) | Microcapsules of the invention | | 1-50% |
| E) | Perfume | Perfume | q.s. |

Procedure:

Heat part A), B) and C) to 85° C. while stirring. When homogeneous, add part B) and C) to A) under agitation. Cool to ambient temperature while stirring and add part D) and E). Homogenize to achieve a small particle size.

What is claimed is:

1. A sunscreen composition, comprising (i) cosmetic adjuvants and additives and (ii) microcapsules with UV filter activity made by a sol-gel method, wherein at least one type of crosslinkable chromophore with UV-A and/or UV-B and/or UV-C filter activity and optionally at least one type of crosslinkable monomer which does not have UV-A and/or UV-B and/or UV-C filter activity are subjected to a crosslinking reaction in the absence of non-crosslinkable chromophores with UV-A and/or UV-B and/or UV-C filter activity, wherein the at least one type of crosslinkable chromophore with UV-A and/or UV-B and/or UV-C filter activity is a monomer of the formula $M(R)_n(P)_m(Q)_q$, wherein M is a metallic or semi-metallic element, R is a hydrolysable group, P is a chromophore with UV-A, UV-B and/or UV-C filter activity, Q is a non hydrolysable group, n is 2 or 3, m is 1 or 2 and q is 0 or 1, and n+m+q=4, and wherein the chromophores are covalently bonded to the polymeric matrix of the microcapsule.

2. The sunscreen composition according to claim 1, wherein at least one type of crosslinkable chromophores with UV-A and/or UV-B and/or UV-C filter activity and at least one type of crosslinkable monomer which does not have UV-A and/or UV-B and/or UV-C filter activity are subjected to a crosslinking reaction in the absence of non-crosslinkable chromophores with UV-A and/or UV-B and/or UV-C filter activity.

3. The sunscreen composition according to claim 1, wherein the chromophore P has the general formula $A-(B)_b(C)_c(D)_d(E)_e$—which is chemically bonded to M wherein A is a chromophore with UV-A and/or UV-B filter activity and $-(B)_b(C)_c(D)_d(E)_e$—is a spacer group in which B is a linear or branched alkylene group with up to 20 carbon atoms C is O, S or NH D is a CONH— group E is a linear or branched alkylene or alkenylene group with up to 20 carbon atoms and b is 0 or 1, c is 0 or 1, d is 0 or 1 and e is 0 or 1.

4. The sunscreen composition according to claim 1, wherein the metallic or semi-metallic element M is silicon.

5. The sunscreen composition according to claim 1, wherein all crosslinkable compounds used for producing the microcapsules are silicon-containing monomers.

6. The sunscreen composition according to claim 1, wherein the at least one type of crosslinkable chromophore with UV-A and/or UV-B and/or UV-C filter activity is a silane monomer comprising at least two $C_{1-6}$-alkoxy groups.

7. The sunscreen composition according to claim 6, wherein all monomers which are used for producing the microcapsules are silane monomers comprising at least two $C_{1-6}$-alkoxy groups.

8. The sunscreen composition according to claim 1, wherein the microcapsules have a particle size of 0.01-100 µm.

9. The sunscreen composition according to claim 1, wherein the amount of crosslinkable chromophores with UV-A and/or UV-B and/or UV-C filter activity is such that the concentration of UV absorber moieties in the final microcapsule is 10-80 w/w %